(12) United States Patent
Wang et al.

(10) Patent No.: US 7,985,234 B2
(45) Date of Patent: Jul. 26, 2011

(54) MEDICAL DEVICE

(75) Inventors: Lixiao Wang, Long Lake, MN (US); Steve Wu, San Diego, CA (US); Ronald A. Sahatjian, Lexington, MA (US); Albert Chin, Newton, MA (US); Peter Dayton, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 318 days.

(21) Appl. No.: 10/083,926

(22) Filed: Feb. 27, 2002

(65) Prior Publication Data

US 2003/0163148 A1 Aug. 28, 2003

(51) Int. Cl.
*A61M 25/10* (2006.01)
(52) U.S. Cl. .................. 606/159; 606/194
(58) Field of Classification Search ........... 606/158, 606/159, 191–194, 200, 170, 195; 604/96.01, 604/103.09, 103.11, 103.12
See application file for complete search history.

(56) References Cited

U.S. PATENT DOCUMENTS

| | | | |
|---|---|---|---|
| 4,273,128 A | 6/1981 | Lary | |
| 4,637,396 A * | 1/1987 | Cook | 606/194 |
| 4,661,110 A | 4/1987 | Fortier et al. | |
| 4,796,629 A * | 1/1989 | Grayzel | 606/194 |
| 4,834,709 A | 5/1989 | Banning et al. | |
| 5,195,969 A | 3/1993 | Wang et al. | |
| 5,196,024 A * | 3/1993 | Barath | 606/159 |
| 5,209,799 A | 5/1993 | Vigil | |
| 5,320,634 A | 6/1994 | Vigil et al. | |
| 5,336,234 A * | 8/1994 | Vigil et al. | 606/159 |
| 5,372,601 A | 12/1994 | Lary | |
| 5,389,314 A | 2/1995 | Wang | |
| 5,458,572 A * | 10/1995 | Campbell et al. | 604/103.08 |
| 5,484,418 A | 1/1996 | Quiachon et al. | |
| 5,533,985 A | 7/1996 | Wang | |
| 5,556,405 A | 9/1996 | Lary | |
| 5,622,665 A | 4/1997 | Wang | |
| 5,649,941 A | 7/1997 | Lary | |
| 5,693,014 A | 12/1997 | Abele et al. | |
| 5,697,944 A | 12/1997 | Lary | |
| 5,704,913 A | 1/1998 | Abele et al. | |
| 5,713,913 A | 2/1998 | Lary et al. | |
| 5,714,110 A | 2/1998 | Wang et al. | |
| 5,792,158 A | 8/1998 | Lary | |
| 5,800,450 A | 9/1998 | Lary et al. | |
| 5,951,494 A | 9/1999 | Wang et al. | |
| 6,117,153 A | 9/2000 | Lary et al. | |
| 6,135,992 A | 10/2000 | Wang | |
| 6,136,258 A | 10/2000 | Wang et al. | |

(Continued)

FOREIGN PATENT DOCUMENTS

EP  0 565 796 A1  10/1992

(Continued)

OTHER PUBLICATIONS

PCT Search Report dated Jul. 23, 2003.

*Primary Examiner* — Ryan J Severson
(74) *Attorney, Agent, or Firm* — Seager, Tufte & Wickhem LLC

(57) ABSTRACT

A medical device includes an inflatable balloon formed having portions of different materials, and a cutting element carried by the balloon. The materials can have different distensibility and/or compliancy.

52 Claims, 3 Drawing Sheets

U.S. PATENT DOCUMENTS

| | | |
|---|---|---|
| 6,242,063 B1 | 6/2001 | Ferrera et al. |
| 6,258,108 B1 | 7/2001 | Lary |
| 6,284,333 B1 | 9/2001 | Wang et al. |
| 6,296,651 B1 | 10/2001 | Lary et al. |
| 6,306,151 B1 | 10/2001 | Lary |
| 6,632,231 B2 * | 10/2003 | Radisch, Jr. .......... 606/159 |
| 6,905,743 B1 * | 6/2005 | Chen et al. .......... 428/35.7 |
| 6,942,680 B2 * | 9/2005 | Grayzel et al. .......... 606/194 |
| 2001/0031357 A1 | 10/2001 | Wang et al. |
| 2001/0033852 A1 | 10/2001 | Wang et al. |
| 2001/0043998 A1 * | 11/2001 | Chen et al. .......... 428/35.7 |
| 2002/0010489 A1 * | 1/2002 | Grayzel et al. .......... 606/194 |
| 2003/0040770 A1 * | 2/2003 | Radisch, Jr. .......... 606/194 |

FOREIGN PATENT DOCUMENTS

| | | |
|---|---|---|
| EP | 0 565 799 A1 | 11/1992 |
| EP | 0 737 488 A4 | 10/1996 |

* cited by examiner

MEDICAL DEVICE

TECHNICAL FIELD

The invention relates to medical devices, such as dilation balloons and catheters having balloons, and methods of making the same.

BACKGROUND

Balloon catheters can be used for a variety of medical procedures such as, for example, to widen an occluded body vessel, as in angioplasty, to position a medical device, such as a stent or a graft, or to selectively block a passageway. A balloon catheter may include an inflatable and deflatable balloon positioned on a long and narrow catheter body. Initially, the balloon is folded around the catheter body to reduce the radial profile of the balloon catheter for easy insertion into the body.

During use, for example, in angioplasty, the folded balloon can be positioned at a location in a vessel occluded by a stenosis by threading the balloon catheter through a guide wire emplaced in the body. The balloon is then inflated, e.g., by introducing a fluid into the interior of the balloon. Inflating the balloon can radially expand the stenosis so that the vessel can permit an increased rate of blood flow. After use, the balloon is deflated and withdrawn from the body.

In some cases, it is desirable to incise at least a portion of the stenosis, e.g., prior to inflating the balloon. Incising the stenosis can further widen the body vessel and increase the rate of blood flow.

SUMMARY

The invention relates to medical devices, such as dilation balloons and catheters having balloons, and methods of making the same.

In one aspect, the invention features a medical device including an inflatable balloon having portions of different materials, and a cutting element carried by the balloon.

Embodiments may include one or more of the following features. The materials have different distensibility, such as along the longitudinal direction of the balloon. The portions extend along the longitudinal direction of the balloon. The cutting element is carried by the balloon over a portion of the balloon having a lower distensibility than another portion of the balloon. The balloon is co-extruded.

The balloon can be formed with a portion having a distensibility less than about 1 mm, e.g., less than about 0.8 mm, less than about 0.5 mm, or less than about 0.3 mm, along the length of the balloon over a predetermined pressure range.

The balloon can be formed with a portion having a distensibility less than about 10%, e.g., less than about 7%, or less than about 5%, along the length of the balloon over a predetermined pressure range.

The pressure range can be from a nominal pressure to a rated burst pressure.

In another aspect, the invention features a medical device including a catheter, an inflatable balloon carried by the catheter, the balloon formed having a striped portion with a lower distensibility than another portion of the balloon, and a cutting element carried by the balloon.

Embodiments may include one or more of the following features. The balloon is formed having a plurality of striped portions. The number of striped portions is greater than the number of cutting elements carried by the balloon. The striped portions are equally spaced around the circumference of the balloon, and/or the striped portion extends parallel to the longitudinal axis of the balloon. The striped portion extends helically about the longitudinal axis of the balloon. The striped portion extends continuously along the length of the balloon.

The striped portion can include a liquid crystal polymer. The striped portion can include a colorant.

The striped portion can extend over a portion of the length of the balloon. The striped portion can extend over substantially the entire length of the balloon.

The cutting element can be carried by the balloon over the striped portion. The cutting element can be carried by the balloon centered over the striped portion.

The balloon can be formed by co-extrusion and/or can be a multi-layered balloon.

The balloon can be formed with a portion having a distensibility less than about 1 mm, e.g., less than about 0.8 mm, less than about 0.5 mm, or less than about 0.3 mm, along the length of the balloon over a predetermined pressure range.

The balloon can be formed with a portion having a distensibility less than about 10%, e.g., less than about 7%, or less than about 5%, along the length of the balloon over a predetermined pressure range.

The balloon can include an inorganic additive.

In another aspect, the invention features a method of making a medical device. The method includes forming a tube having a striped portion with a lower distensibility than another portion of the tube, forming an inflatable balloon from the tube, and attaching a cutting element to the balloon.

The tube can be formed by co-extrusion and/or by lamination.

The cutting element can be attached to the balloon with an adhesive. The cutting element can be attached to the balloon over the striped portion.

The method can further include folding a portion of the balloon over the cutting element.

In another aspect, the invention features an extrusion apparatus including a first disc having a first inlet and a first outlet in fluid communication with the first inlet, the first disc configured to permit flow of a first material therethrough, and a second disc having a second inlet, a second outlet in fluid communication with the second inlet, and a plurality of passageways in fluid communication with the second inlet and the second outlet, the second disc configured to permit flow of a second material different than the first material therethrough. The first and second discs are configured to form a member having discrete portions of the second material separated by the first material.

Embodiments may include one or more of the following features. The plurality of passageways is in fluid communication with the first outlet. The apparatus further includes a third disc having a third inlet and a third outlet configured to permit flow of the first material therethrough. The second disc is between the first and third discs. The first and second materials comprise a polymer. The apparatus is a disc head extrusion apparatus. The apparatus is configured to be used in the fabrication of a polymer tube having a striped portion.

In another aspect, the invention features a method of extrusion. The method includes flowing a first material through a first disc having a first inlet and a first outlet in fluid communication with the first inlet, flowing a second material different than the first material through a second disc having a second inlet, a second outlet in fluid communication with the second inlet, and a plurality of passageways in fluid communication with the second inlet and the second outlet, and forming a member having discrete portions comprising the second material separated by the first material.

Embodiments may include one or more of the following features. The method further includes flowing the first material through a third disc having a third inlet and a third outlet in fluid communication with the third inlet. The method further includes rotating the member about the longitudinal axis of the member. The discrete portions extend along the longitudinal axis of the member. The member is a polymer tube.

In another aspect, the invention features a medical device including an inflatable balloon having portions of different materials, wherein at least one portion extends helically about the longitudinal direction of the balloon.

Embodiments may include one or more of the following features. The materials have different distensibility. The balloon includes two portions of different material, and both portions extend helically about the longitudinal direction of the balloon. At least one portion includes a liquid crystal polymer. The balloon is co-extruded. At least two portions include a material of the same composition.

In yet another aspect, the invention features a medical device including an inflatable balloon having a discrete portion of material extending helically about the longitudinal direction of the balloon.

Embodiments may include one or more of the following features. The discrete portion has a chemical composition different than another portion of the balloon. The discrete portion includes a liquid crystal polymer. The discrete portion has a higher flexural modulus than another portion of the balloon. The balloon has a first portion with a first density of the discrete portion higher than a second density of the discrete portion of a second portion of the balloon. The first portion is a tapered portion of the balloon and/or a sleeve portion of the balloon.

In another aspect, the invention features a method of making a medical device including forming a tube having a discrete portion of material extending helically about the longitudinal direction of the tube, and forming an inflatable balloon from the tube.

Embodiments may include one or more of the following features. The tube is formed by co-extrusion and/or lamination. The inflatable balloon is formed by blow molding.

Other features and advantages of the invention will be apparent from the description of the preferred embodiments thereof and from the claims.

DETAILED DESCRIPTION

Figure 1:
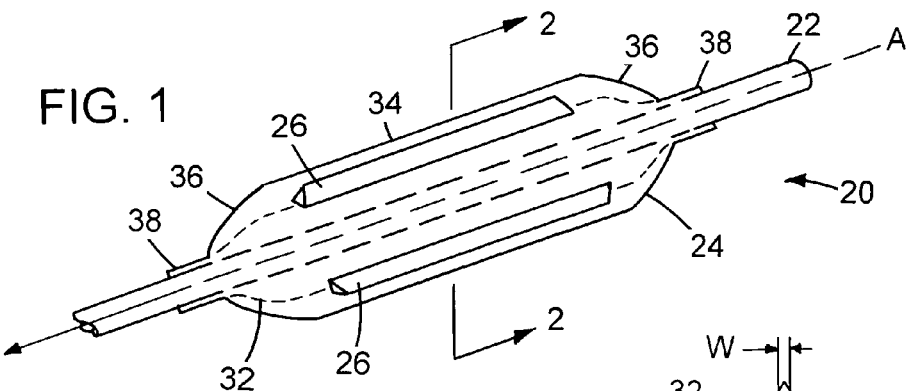
FIG. 1 is an illustration of an embodiment of a medical device.
Figure 2:
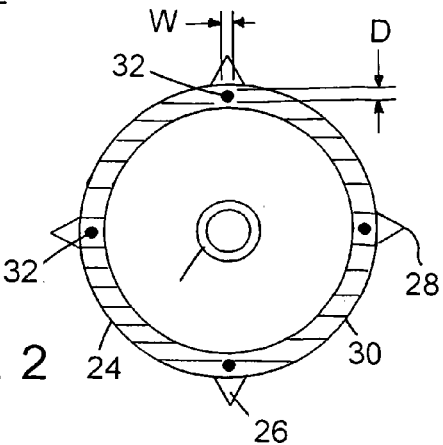
FIG. 2 is a cross sectional view of the medical device of FIG. 1, taken along line 2-2.

Referring to FIGS. 1 and 2, a balloon catheter 20 includes a catheter body 22, an inflatable balloon 24 attached to the catheter body, and a plurality of cutting elements 26 (here, four) attached to the balloon, for example, by an adhesive such as a urethane. Medical devices such as balloon catheter 20 are described in, for example, Wang U.S. Pat. No. 5,195,969, and Hamlin U.S. Pat. No. 5,270,086, both hereby incorporated by reference; and are exemplified by the Ranger® system available from Boston Scientific Scimed, Maple Grove, Minn. Cutting elements 26 are elongated members (e.g., steel blades) having a triangular cross section in which the base is attached to balloon 24 and a cutting edge 28 is formed at the apex of the triangular section. Examples of cutting elements 26 are described in Vigil U.S. Pat. Nos. 5,209,799 and 5,336,234, both hereby incorporated by reference.

Referring particularly to FIG. 2, balloon 24 is co-extruded from a matrix material 30 and discrete (e.g., individually distinct) striped portions 32 (here, four) surrounded by the matrix material. Cutting elements 26 are attached to balloon 24 over striped portions 32. In embodiments, striped portions 32 are formed of a material(s) having a lower compliancy than material(s) that are not in the striped portions, such as those of matrix material 30. Alternatively or in addition, striped portions 32 are formed of a material(s) having a lower distensibility than material(s) that are not in the striped portions. Compliancy and distensibility may apply to the radial direction and/or the longitudinal direction of balloon 24. Alternatively or in addition, striped portions 32 are stiffer, harder, and/or stronger than non-striped portions of balloon 24.

In some embodiments, striped portions 32 have relatively low longitudinal distention, for example, during use of balloon 24. Striped portions 32 may elongate less than 1 mm (e.g., less than 0.8 mm, less than 0.6 mm, less than 0.4 mm, less than 0.2 mm, less than 0.1 mm, or less than 0.05 mm) over a nominal length of balloon 24. Alternatively or in addition, striped portions 32 may elongate less than 12% (e.g., less than 10%, less than 8%, less than 6%, less than 5%, less than 3%, less than 2%, less than 1%, less than 0.5%, less than 0.4%, less than 0.3%, less than 0.2%, or less than 0.01%, or about zero) over a nominal length of balloon 24. The amount of elongation can be measured over a predetermined pressure range, such as from a starting, deflated balloon pressure to a final, inflated pressure during use, or from a nominal pressure to a rated burst pressure. In some embodiments, the degree of elongation described herein applies to the radial direction.

Without wishing to be bound by theory, it is believed that attaching cutting elements 26 over striped portions 32 (e.g., areas relatively low compliancy and/or distensibility) enhances the attachment between the cutting elements and balloon 24. For example, as balloon 24 is inflated (e.g., up to 10 atm or higher) and deflated during use, striped portions 32 are less likely to change, e.g., grow or distend, longitudinally and/or radially, relative to non-striped portions of the balloon, such as compliant portions made of the matrix material. The interface between cutting elements 26 and striped portions 32 can remain relatively constant during use. As a result, mechanical stress between cutting elements 26 and balloon 24 reduced, and attachment therebetween is enhanced.

Figure 3:
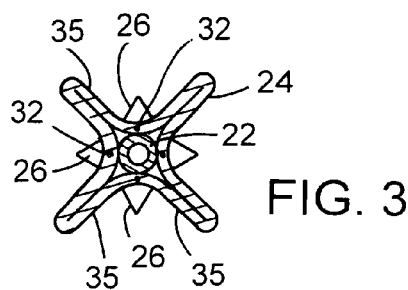
FIG. 3 is a cross sectional view of an embodiment of a medical device.

Furthermore, it is believed that striped portions 32 also enhance folding and refolding of balloon 24. A striped portion 32 and areas adjacent to the striped portions can behave like a hinge. For example, referring to FIG. 3, a (relatively non-compliant) striped portion 32 can act as a stationary member of a hinge and the (relatively compliant) adjacent areas 35 can act as moveable members of the hinge that pivot about the interfacial region between the striped portion and the adjacent areas 35. When balloon 24 is deflated, it can fold along the interfacial region so that compliant areas 35 form flaps, and striped portions 32 are positioned in furrows. As a result, balloon 24 can be formed and used with a relatively low profile and a relatively predictable folding configuration, thereby providing desirable insertion and withdrawal of catheter 20 from the subject.

Balloon 24 can have any number of striped portions 32, depending, for example, on the number of cutting elements 26 to be attached to the balloon and the desired folding configuration. Balloon 24 can have one or more striped portion 32, e.g., 2, 3, 4, 5, 6, 8 or more. The number of striped portions 32 that balloon 24 includes can be different than the number of cutting elements 26 attached to the balloon. For example, balloon 24 may include 8 striped portions 32 formed equally spaced around the balloon, and 4 cutting elements 26 attached equally spaced around the balloon, with each cutting element attached over a striped portion. That is, balloon 24 has a cutting element attached over every other striped portion 32. In some embodiments, forming catheter 20 with more striped portions 32 than cutting elements 26 may enhance folding of balloon 24, and/or reduce radial and/or longitudinal growth of the balloon during use.

Striped portions 32 can be equally and/or unequally spaced around the circumference of balloon 24. For example, looking at a radial cross section (e.g., FIG. 2) of balloon 24 having six striped portions 32, the striped portions can be formed at 2 o'clock, 3 o'clock, 4 o'clock, 8 o'clock, 9 o'clock, and 10 o'clock. Striped portion 32 at 3 o'clock is equally spaced from striped portions at 3 o'clock and 4 o'clock; but, for example, striped portion at 4 o'clock is unequally spaced from striped portions at 3 o'clock and 8 o'clock. Striped portions 32 can be symmetrically or asymmetrically positioned around the circumference of balloon 24.

The dimensions of striped portions 32 can vary. Striped portions 32 can have a thickness or diameter D (FIG. 2) as large as the wall thickness of balloon 24 to about 5% of the wall thickness. For example, diameter D can be about 10%, 20%, 30%, 40%, 50%, 60%, 70%, 80%, or 90% of the wall thickness of balloon 24. In some embodiments, the diameter of striped portions 32 can range from about 1 mil to about 10 mil, depending on the wall thickness of the tube from which balloon 24 is formed, e.g., blow molded. Similarly, striped portions 32 can have a width that varies, for example, from less than the width of a cutting element 26 to greater than the width of the cutting element. The dimensions of striped portions 32 can be dependent on the rigidity, hardness, compliancy, etc, of the materials used in the striped portions. For example, smaller widths can be used when the material(s) is relatively highly rigid. The dimensions of striped portions 32 can be optimized for a given balloon 24 and/or cutting element 26. Striped portions 32 can extend for substantially the entire length of balloon 24 or selected portions of the balloon. Striped portions 32 may extend through body portion 34 of balloon 24, through one or more tapered portion 36, and/or through one or more sleeve portion 38. For example, striped portions 32 may extend through only tapered portions 36 and body portion 34. Different cross sectional profiles for striped portions 32 can be used. For example, striped portions 32 can have a cross section that is circular, oval, dumbbell-shaped, or polygonal, e.g., having 3, 4, 5, 6 or more sides. The cross section can be regular or irregular. Different combinations of dimensions of striped portions 32 can be used.

Figure 4:
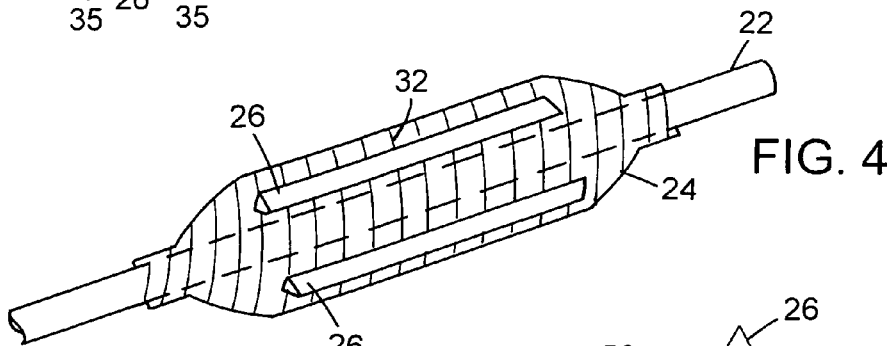
FIG. 4 is an illustration of an embodiment of a medical device.

Different arrangements or configurations of striped portions 32 are possible. Striped portions 32 can extend parallel to the longitudinal axis A of balloon 24 (FIG. 1). Striped portions 32 can extend helically around longitudinal axis (FIG. 4). For example, a co-extruded tube can be formed with helically oriented striped portions 32, and blow molded to form balloon 24. As a result, portions of balloon 24 that have been expanded more than other portions of the balloon can have a lower density of striped portions 32 (number of striped portions per unit length). That is, in certain embodiments of balloon 24, body portion 34 can have the lowest density of striped portions 32, followed by tapered portions 36, and followed by sleeve portions 38 with the highest density of striped portions. It is believed that this configuration of striped portions 32 can further restrict radial and/or longitudinal growth of balloon 24, while allowing the balloon to be inflated radially. Striped portions 32 can extend continuously or non-continuously along a predetermined length. For example, a striped portion extending along the length of balloon 24 can be composed of multiple, interrupted striped portions arranged collinearly, i.e., end to end. Combinations of different configurations are possible. For example, balloon 24 may include parallel striped portions 32 that are continuous and non-continuous. Striped portions that are under cutting elements 26 can have the same or different dimensions and/or configurations than striped portions not under the cutting elements.

As described above, in embodiments, striped portions 32 are formed of relatively non-compliant, stiff, hard, and/or strong materials. Striped portions 32 can have relatively low distensibility. In some embodiments, striped portions 32 are formed of material(s) having a compliancy less than about 12% (e.g., less than 10%, less than 8%, less than 6%, less than 4%, or less than 25). Examples of materials that can be used for striped portions 32 include polyethylene terephthalate (PET) (e.g., MELINAR® 5922C or CLEARTUF® 8066), polyethylene naphthalate (PEN), aromatic nylons, rigid polyurethanes, polyesters, copolyesters, polyester blends, polyester/polyurethane blends, polyetheretherketone (PEEK), polyphenyl sulfide (PPS), and fluoropolymers.

In some embodiments, striped portions 32 have a flexural modulus of about 150,000 psi to about 3,000,000 psi. The flexural modulus can be greater than or equal to about 200,000 psi, 500,000 psi, 1,000,000 psi, 1,250,000 psi, 1,500,000 psi, 2,000,000 psi, or 2,500,000 psi; and/or less than or equal to about 2,500,000 psi, 2,000,000 psi, 1,500,000 psi, 1,250,000 psi, 1,000,000 psi, 500,000 psi, or 200,000 psi. In preferred embodiments, the flexural modulus of striped portions 32 is greater than the flexural modulus of matrix material 30.

In some embodiments, striped portions 32 include a liquid crystal polymer (LCP) (e.g., a composite material having the LCP incorporated therein). The LCP preferably has good miscibility and/or compatibility with other materials (e.g., polyamides or polyesters) in striped portions 32. The LCP preferably has a relatively low melting temperature for convenient handling and processing. Examples of LCPs include polyester(s), polyamide(s), their blends, and/or their copolymers, such as VECTRA® A (Ticona), VECTRA® B (Ticona), VECTRA® LKX (Ticona) (e.g., VECTRA® LKX 1107, 1111 (Ticona)), and VECTRAN® (e.g., VECTRAN V300P (Ticona)). Other LCPs and/or combinations of LCPs can be used.

The LCP can be incorporated into one or more polymers as described herein, such as, for example, a PEBA-type (polyether-block-amide) type material, such as PEBAX®, Grilon, Grilamid and/or Vestamid, a nylon, a thermoplastic polyester and/or thermoplastic elastomer versions thereof. In certain embodiments, an LCP-containing composition can be relatively stiff in the direction of melt flow. Without wishing to be bound by theory, it is believed that this may result because LCP crystals (e.g., fibers) form or align in the melt flow direction as the polymer composite cools from a liquid state to a solid state. It is believed that the LCP fibers can reinforce the other polymer(s) contained in surrounding portions (e.g., matrix polymer(s)), which can restrict a balloon from growing in length during inflation while permitting the balloon to be inflated. Methods of blending LCP-containing materials, including extrusion techniques and other examples of LCPs, are described in Ferrera U.S. Pat. No. 6,242,063, and Wang U.S. Pat. No. 6,284,333, both hereby incorporated by reference.

The amount of LCP contained in striped portions 32 can vary depending upon its intended use. The LCP content of striped portions 32 can be about 1 to about 5 weight percent. The LCP content of striped portions 32 can be greater than or equal to about 1.0%, 1.5%, 2.0%, 2.5%, 3.0%, 3.5%, 4.0%, or 4.5% weight percent; and/or less than or equal to about 5.0%, 4.5%, 4.0%, 3.5%, 3.0%, 2.5%, 2.0%, or 1.5% weight percent.

Striped portions 32 within a balloon 24 can be formed of different materials. For example, striped portions 32 under cutting elements 26 can be formed of different materials than striped portions that are not under a cutting element. Striped portions 32 can be formed of the same or similar material(s).

In some embodiments, striped portions 32 include an additive. The additive can be a pigment that reinforces striped portions 32. Examples of additives include non-polymeric, inorganic additives such as titanium oxides, such as $TiO_2$, calcium carbonate, mica, aramide fibers, carbon black, glass, or fiberglass. Thus, striped portions 32 can be formed of the same material(s) as matrix material 30 having an additive (such as an LCP(s) or the additive(s) described above) to increase the rigidity, flexural modulus, strength, and/or hardness. The additive can decrease distention and/or compliancy.

In some embodiments, striped portions 32 may include a colorant that can be used to detect the striped portions for attaching cutting elements 26 to balloon 24. Examples of colorants include acid dyes (e.g., monoazo or anthraquinone dyes), basic dyes (e.g., C.I. Basic Blue 3 or C.I. Basic Green 4), ionic (i.e., acid and basic) and disperse dyes, such as those listed in "Dyes and Pigments by Color Index and Generic Names" in Textile Chemist and Colorist, 24 (7), 1992.

Matrix material 30 for balloon 24 can be any compliant or semi-compliant material capable of allowing the balloon to be inflated radially. Matrix material 30 is preferably relatively soft and flexible. As a result, matrix material 30 can also provide balloon 24 with good re-fold characteristics, e.g., after the balloon has been inflated and deflated, and good trackability and crossability through a body lumen. In some embodiments, the matrix material has a compliancy of greater than 5% growth (e.g., greater than 10%) over a predetermined pressure range (e.g., from atmospheric pressure to a rated burst pressure).

Examples of materials that may be used as the matrix material include polyurethanes and block copolymers, such as polyamide-polyether block copolymers or amide-tetramethylene glycol copolymers. Examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can be used. Still other examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® have a Shore D hardness of about 45D to about 82D.

The matrix materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer.

In some embodiments, matrix material 30 has a flexural modulus of about 20,000 psi to about 250,000 psi. The flexural modulus can be greater than or equal to about 20,000 psi, 50,000 psi, 100,000 psi, 125,000 psi, 150,000 psi, 175,000 psi, 200,000 psi, 220,000 psi, or 250,000 psi; and/or less than or equal to about 250,000 psi, 220,000 psi, 200,000 psi, 175,000 psi, 150,000 psi, 125,000 psi, 100,000 psi, or 50,000 psi.

Matrix material 30 can include one or more LCPs, as described herein.

In some embodiments, the matrix material may include an additive that decreases compliancy. The additive can be a pigment that reinforces matrix material 30. Examples of additives include inorganic additives such as titanium oxides, such as $TiO_2$, calcium carbonate, mica, aramide fibers, carbon black, glass, or fiberglass.

In some embodiments, a compatibilizing material can be incorporated into balloon 24. Without wishing to be bound by theory, it is believed that in some circumstances, striped portions 32 and matrix material 30 may be incompatible to a sufficient degree that phase separation may occur. As a result, slippage between phases may occur during balloon expansion that reduces the longitudinal restriction effect of stripes portions 32. A compatibilizing material may reduce such slippage by enhancing the homogeneity of the melt blend prior to extrusion and cooling. For example, the compatibilizing material may be added to a pre-extruded melt blend to provide a more indistinct phase boundary between a stripe component, e.g., an LCP, and a matrix component. The compatibilizing material can be designed, for example, to modify one or more phase boundaries of the LCP(s) and one or more of the other polymer(s) (e.g., thermoplastic polymer(s)) and/or to enhance adhesion between the LCPs and one or more of the other polymer(s). The compatibilizing material can be a copolymer, such as a block copolymer, including moieties of at least two different chemical structures, respectively providing compatibility with an LCP and one or more other polymers in the mixture. The compatibilizing material can be a reactive polymer that reacts with the LCP and/or one or more other polymers in the mixture. The compatibilizing material can be a catalyst that promotes a reaction between the LCP and one or more other polymers in the mixture.

Examples of compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl(meth)acrylate-ethylene-glycidyl (meth)acrylate polymers) can be used. Ionomeric copolymers can be used. PETG can be used. Examples of compatibilizing materials include Hytrel HTR-6108, Polybond 3009 (BP Chemicals), SP 2205 (Chevron), DS 1328/60 (Chevron), Lotader 2400, Escor ATX-320, Escor ATX-325, Vamac G1 and Lotader AX8660. In certain embodiments, a compatibilizing material (e.g., PETG) can be mixed with one or more polymers (e.g., an LCP-containing material) prior to extrusion. Other compatibilizing materials can be used. Combinations of compatibilizing materials can be used.

However, in some embodiments, including where balloon materials are relatively incompatible, a compatibilizing material may not be needed. Without wishing to be bound by theory, it is believed that in certain circumstances, e.g., certain dimensions and/or configurations of striped portions 32, the striped portions can be mechanically encapsulated or trapped by matrix material 30 such that a balloon can be formed even when the matrix material and striped portion material are relatively incompatible or have relatively low affinity for each other. That is, striped portions 32 need not necessarily bond with the matrix material. As an example, a balloon can be formed with PET striped portions and PE as the matrix material.

As with striped portions 32, balloon 24 can have various numbers of cutting elements 26, of different spacing, configurations, and/or dimensions. Balloon 24 can have one more cutting elements 26, e.g., 2, 3, 4, 5, 6, 8 or more. One or more cutting elements 26 can be placed centered or off-centered over one or more striped portions 32. Cutting elements 26 can be equally and/or unequally spaced around the circumference of balloon 24. Cutting elements 26 can extend continuously and/or non-continuously along portions of balloon 24. For example, a line of cutting element 26 can be formed of a plurality of cutting elements arranged end to end. Combinations of different spacings, configurations and/or dimensions are possible. Cutting elements 26 can have smooth and/or jagged, e.g., serrated, cutting edges 28. Cutting elements 26 can be formed of a polymer, such that those described above having sufficient hardness, stiffness, and/or strength. A polymeric cutting element may include an LCP, as described above. A polymeric cutting element may be formed by molding and then attached to balloon 24 using an adhesive.

Balloon 24 can be formed from a tube or parison formed by an extrusion process, such as by disc co-extrusion. An example of disc co-extrusion is described in commonly assigned application U.S. Ser. No. 09/798,749, filed Mar. 2, 2001, and entitled "Multilayer Medical Device". This process can generally involve using an extrusion apparatus (e.g., a crosshead, such as a compact crosshead) having a series of discs. Each disc can have one or more appropriately designed channels. The number of channels can be selected based on, for example, the number of striped portions 32, the volumetric output, the temperature, the viscosity, the pressure drop, the outer diameter of the discs, the material (e.g., polymer(s)) used, and/or the channel dimensions.

As described in U.S. Ser. No. 09/798,749, extrusion is performed using an extrusion apparatus (a compact crosshead) having a series of extrusion discs that selectably receive different polymers from separate extruders, e.g., one containing matrix material and one containing material for the striped portions. Generally, each of the disc include passageways for both polymers but an extrusion inlet and outlet for only one of the materials. In this way, polymer flow continues along the series of discs but each polymer is added to the extrusion stream in a desired order.

Figure 7A:
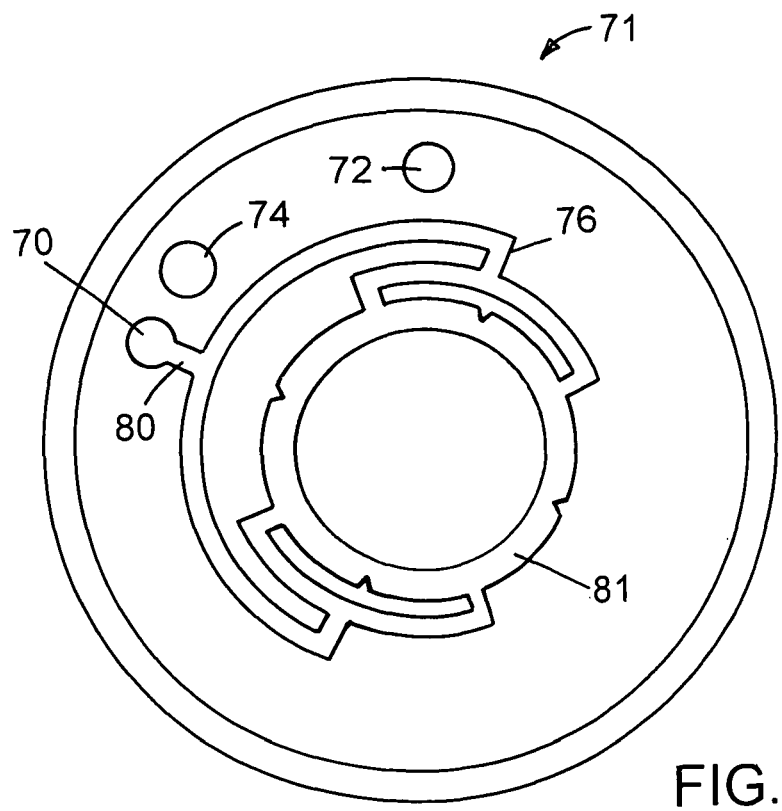
FIGS. 7A, 7B, and 7C are cross sectional views of an inner, a middle, and an outer crosshead disc, respectively, according to one embodiment.
Figure 7B:
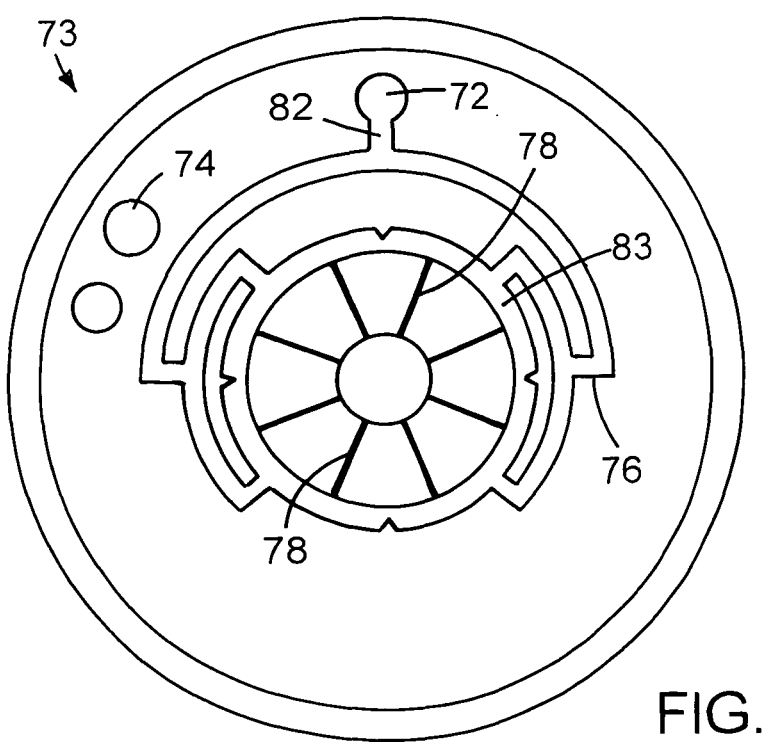
Figure 7C:
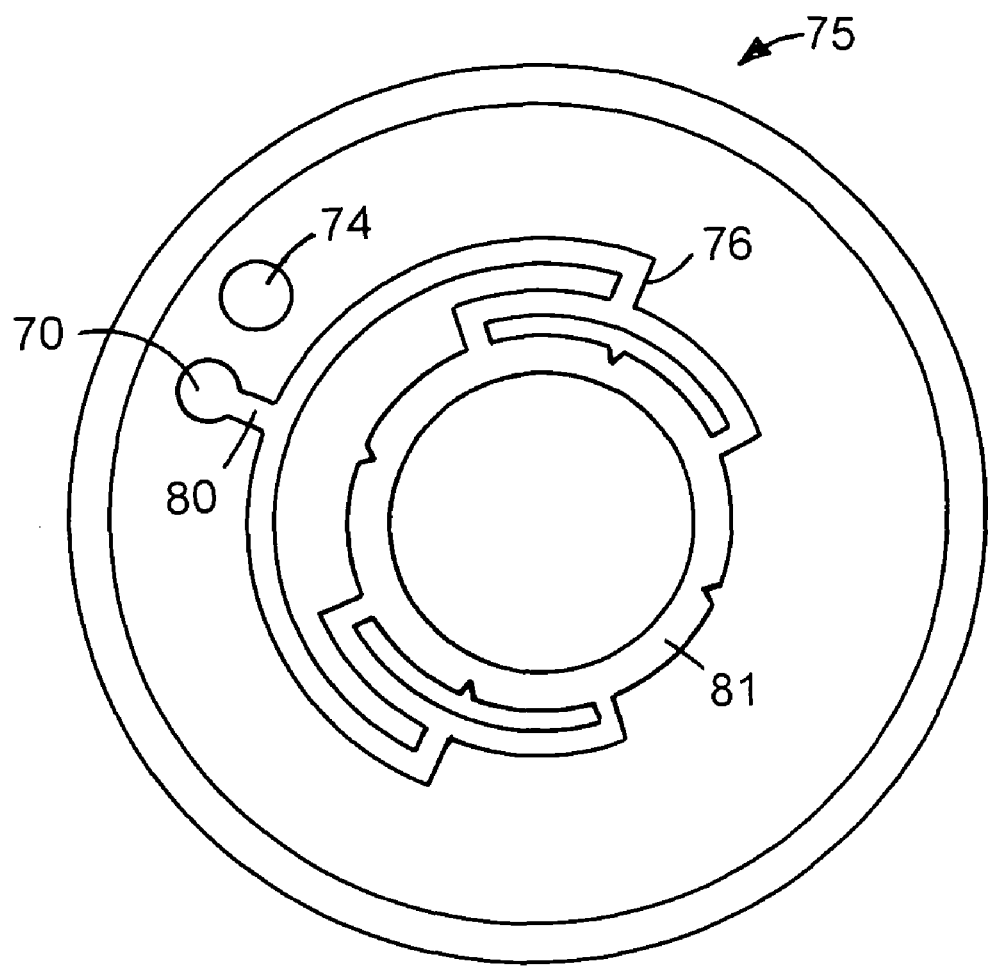

FIGS. 7A-7C show three four-channel disc (inner disc 71, middle disc 73, and outer disc 75, respectively) designs that can be used together in a crosshead to form a tube having eight striped portions. The inlets and outlets of the discs are formed as machined channels in the face of the discs. For example, matrix material flows through passageway 70, and striped portion material flows through passageway 72. (An opening 74 for an alignment pin is provided for registration of the discs.) Inner disc 71 and outer disc 73 have an inlet 80 and an outlet 81 for the matrix material. The outlets are formed by channels 76 that lead to gaps between adjacent discs. Discs 71 and 75 have a passageway 72 for the striped portion material but not inlet or outlet for striped portion material. Middle disc 73 has an inlet 82 and an outlet 83 for the striped portion material but no inlet or outlet for the matrix material. Middle disc 73 further includes eight passageways 78 in fluid communication with outlet 83 for forming the striped portions. As a result, when discs 71, 73, and 75 are placed together, the striped portion material will be encapsulated by the matrix material after extrusion, thereby forming a tube with striped portions. In other embodiments, different combinations and arrangements of discs can be used, as described in U.S. Ser. No. 09/798,749.

Prior to co-extrusion, a stock of striped portions 32 is formed using twin screw compounding, which provides good dispersion. For example, to form materials for a striped portion having 2% Vectran V300P in Vestamid, a master batch of 20% Vectran V300P and 80% Vestamid is compounded in a co-rotating twin screw extruder (34 mm, Leistriz) and chopped into pellets. The pellets are then dry blended by hand with sufficient virgin Vestamid to dilute the concentration to 2% Vectran V300P, and fed into a single screw extruder. An example of a compounding condition include a melt temperature of about 250° C., a screw speed of about 150 rpm, and a feed rate of about 15 lbs/hour.

A dual extrusion process using two extruders (e.g., two single screw extruders) is used to form a desired tube, for example, as described in U.S. Ser. No. 09/798,749. In addition, other extrusion techniques are described, for example, in Ferrera U.S. Pat. No. 6,242,063; Wang U.S. Pat. No. 6,284,333; and Wang U.S. Pat. Nos. 6,135,992; 5,951,494; and 5,389,314, all hereby incorporated by reference. Methods for forming discrete, helically oriented striped portions, are described, for example, in U.S. Ser. No. 09/898,710, filed Jul. 3, 2001, hereby incorporated by reference in its entirety.

In some embodiments, if relative rotation of an extrusion mandrel and die is avoided during extrusion, then LCP fibrils can adopt an orientation substantially parallel to the longitudinal axis. If the die and mandrel are relatively rotated, e.g., by rotation of one or both, the orientation of the fibrils may be helical about the longitudinal axis. In some embodiments, the shear rate can be adjusted to provide sufficient force to shear LCP(s) into fibrils. These types of extrusion techniques are described, for example, in U.S. Patent Application Publication No. 2001/0043998 A1, Nov. 22, 2001, hereby incorporated by reference.

To form balloon 24, the formed (e.g., co-extruded) tube can be blow molded. In some embodiments, the tube is placed in a preheated balloon mold, and air is introduced into the tube to maintain the patency of the tube lumen. After soaking at a predetermined temperature and time, the tube is stretched for a predetermined distance at a predetermined time, rate, and temperature. The pressure inside the tube is then sufficiently increased to radially expand the tube inside the mold to form the balloon. The formed balloon can be heat treated, for example, to enhance folding memory, and/or folded into a predetermined profile. Methods of forming a balloon from a tube are described in, for example, commonly-assigned U.S. Ser. No. 09/950,195, filed Sep. 10, 2001, and entitled "Medical Balloon"; Anderson U.S. Pat. No. 6,120,364; Wang U.S. Pat. No. 5,714,110; and Noddin U.S. Pat. No. 4,963,313, all hereby incorporated by reference in their entirety.

Figure 5:
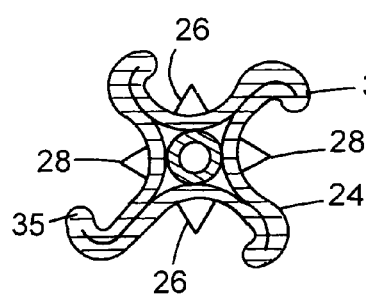
FIG. 5 is a cross sectional view of an embodiment of a medical device.

After the balloon is formed, cutting elements 26 can be attached to the balloon, e.g., patches of an adhesive, to form balloon 24. Balloon 24 can be folded (FIG. 3) using the methods described in Vigil U.S. Pat. No. 5,209,799. In some cases, referring to FIG. 5, the relatively compliant areas, e.g., flaps 35, can be folded over cutting elements 26 to protect a body lumen from cutting edges 28. Folding can be performed by engaging, e.g., grasping, flaps 35 with a chuck, and rotating the chuck. Folding can be performed during heat treatment of balloon 24, as described in Vigil U.S. Pat. No. 5,209,799.

Other Embodiments

In other embodiments, balloon 24 and/or catheter body 22 can be have a wall composed of a plurality of layers formed of polymers. Multilayer devices are described in Hamlin U.S. Pat. No. 5,270,086; Wang U.S. Pat. No. 5,195,969; Hamilton U.S. Pat. No. 5,797,877; and U.S. Ser. No. 09/798,749, all hereby incorporated by reference in their entirety. The layers can be selected to provide catheter body 22 and/or balloon 24 with desired properties.

Figure 6:
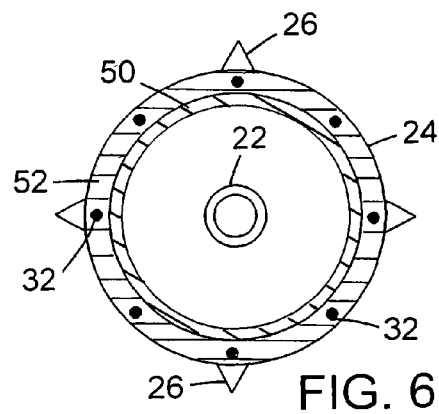
FIG. 6 is a cross sectional view of an embodiment of a medical device.

For example, referring to FIG. 6, balloon 24 can include an inner layer 50, an outer layer 52, and striped portions 32 extending through the outer layer. Inner layer 50 can be formed of PEBAX 7223 to provide tensile strength; outer layer 52 can be formed of PEBAX 40-50D to provide a soft outer surface and to protect striped portions 32; and striped portions 32 can include an LCP(s) as described herein.

Different combinations of layering, e.g., materials, sequence, and/or thickness, can be used as described in U.S. Ser. No. 09/798,749. Striped portions 32, as described herein, can be in any combinations of the formed layer(s).

Other methods of forming balloon 24 with striped portions 32 are possible. For example, a tube having different materials can be formed by lamination. A tube made of a matrix material can be laminated, e.g., using an adhesive, with strips of material suitable for striped portions 32. As the tube is radially expanded (e.g., blow molded) to form a balloon, the strips of material tend to blend with the matrix material, i.e., become more indistinct. Cutting elements 26 can then be attached over the strips. The strips of materials can have, e.g., similar configurations and/or dimensions as striped portions 32.

Other non-extrusion processes can also be used to form striped portions 32 or non-striped portions. For example, mechanically working (e.g., thumping) selected portions of a tube, e.g., the matrix material, can alter (e.g., increase) its compliancy, toughness, hardness, etc. Striped portions 32 (or non-striped portions) can be formed by irradiating selected portions of the matrix material, e.g., with an ion beam or an electron beam. Striped portions 32 (or non-striped portions) can be formed by chemically treating selected portions of the matrix material, e.g., by masking certain portions and treating unmasked portions with a cross-linking agent.

Other methods of attaching cutting elements 26 to balloon 24 are possible. Cutting elements 26 may be thermally and/or mechanically bonded. For example, cutting elements 26 may include projections, e.g., hooks, at their base that embed into the wall of balloon 24. The projections can be embedded manually. The cutting elements can be appropriately positioned in the balloon-forming mold with the projections extending into the cavity of the mold. The projections are embedded into the wall of the balloon as a tube is radially expanded to form the balloon.

The following examples are illustrative and not intended to be limiting.

Example 1

The following examples illustrate extrusion conditions for forming a tube or parison.

A tube for making a 3.5-mm balloon having Nylon 12 matrix material and 8 striped portions (2.5% LCP/97.5% Nylon 12) was extruded. For the matrix material, the melt temperature was 510° F., and the screw (1 inch diameter screw) speed was 25 rpm, with no gear pump. For the LCP, the melt temperature was 490° F., and the pump speed was 3 rpm, with a 0.6 cc/rev pump. The line speed was 38 fpm.

Example 2

A tube for making a 7-mm balloon having Nylon 12 matrix material and 4 striped portions (2.5% LCP/97.5% Nylon 12) was extruded. For the matrix material, the melt temperature was 525° F., and the screw (1 inch diameter screw) speed was 18 rpm, with no gear pump. For the LCP, the melt temperature was 500° F., and the pump speed was 2 rpm, with a 0.6 cc/rev pump. The line speed was 22 fpm.

Example 3

The following example illustrates a process for forming a balloon.

A tube or parison (0.054" O.D.×0.031"I.D.) formed by the methods described herein was placed into a 4.0×12 mm balloon mold preheated to about 260° F. The tube was then held at the both ends, and air was injected into the tube at about 200 psi to prevent the tube from collapsing under heat. The tube was heated in the mold for about 25 sec, and then pulled by both ends at a speed of 5 mm/sec for a distance of 18 mm on each end. Each end was then allowed to spring back (i.e., contract) about 6 mm. While the tube was pulled, the air pressure inside the tube was increased to about 400 psi. At this stage, the tube typically formed into the balloon body. The tube was held at 260° F. and about 400 psi for about 3 sec. The air pressure was then increased to 420 psi for a second pulling step.

The tube was again pulled for a distance of 18 mm over 3 sec to enhance the balloon tapered areas and sleeves. The tube was then kept at about 430 psi for 9 sec to enhance shape memory of the balloon. The mold was then opened to remove the formed balloon. The formed balloon was then taken out for dimensional measurements and testing, e.g., burst strength measurements.

Generally, balloon-forming parameters are a function of, for example, the tube (e.g., the tube size and materials) and the balloon being formed (e.g., the balloon size, parallel stripes vs. helical stripes). For example, the mold temperature can range from about 200 to about 350° F. The injected air pressure can range from about 120 psi to about 450 psi. The pull distance can range from about 5 mm to about 30 mm. The heating soak time for the tube and the balloon can range from about 3 sec to about 40 sec.

A balloon having helically extending striped portions can be formed by extruding a tube having helically-extending portions, as described above and in U.S. Ser. No. 09/898,710, and forming a balloon as described above or in the incorporated-by-reference applications, publications, and patents.

All publications, applications, and patents mentioned in this application are herein incorporated by reference to the same extent as if each individual publication or patent was specifically and individually indicated to be incorporated by reference in their entirety.

Other embodiments are within the claims.

What is claimed is:

1. A medical device, comprising:
    a repeatably inflatable and deflatable balloon including a body portion, a first sleeve portion, a second sleeve portion, a first tapered portion located between the first sleeve portion and the body portion, and a second tapered portion located between the second sleeve portion and the body portion, the balloon having a first material and a discrete strip of a second material extending continuously from a first end of the discrete strip of the second material to a second end of the discrete strip of the second material, the discrete strip of the second material being encapsulated by the first material when the balloon is inflated, the discrete strip of the second material extending continuously along the body portion of the balloon into the first tapered portion and into the second tapered portion, the second material having a lower distensibility and a higher stiffness than the first material; and
    a cutting element carried by the balloon centered over the discrete strip of the second material;
    wherein portions of the balloon formed of the first material that are adjacent to the discrete strip form flaps each time the balloon is deflated such that the cutting element is located in a furrow between flaps of the balloon.

2. The device of claim 1, wherein the materials have different distensibility along the longitudinal direction of the balloon.

3. The device of claim 1, wherein the discrete strip of the second material extends along the longitudinal direction of the balloon.

4. The device of claim 1, wherein the balloon is formed with a portion having a distensibility less than about 1 mm along the length of the balloon over a predetermined pressure range.

5. The device of claim 1, wherein the balloon is formed with a portion having a distensibility less than about 0.8 mm along the length of the balloon over a predetermined pressure range.

6. The device of claim 1, wherein the balloon is formed with a portion having a distensibility less than about 0.5 mm along the length of the balloon over a predetermined pressure range.

7. The device of claim 1, wherein the balloon is formed with a portion having a distensibility less than about 0.3 mm along the length of the balloon over a predetermined pressure range.

8. The device of claim 1, wherein the balloon is co-extruded.

9. The device of claim 1, wherein the balloon is formed with a portion having a distensibility less than about 10% along the length of the balloon over a predetermined pressure range.

10. The device of claim 1, wherein the balloon is formed with a portion having a distensibility less than about 7% along the length of the balloon over a predetermined pressure range.

11. The device of claim 1, wherein the balloon is formed with a portion having a distensibility less than about 5% along the length of the balloon over a predetermined pressure range.

12. The device of claim 1, wherein the cutting element is spaced from the discrete strip of the medical material.

13. The medical device of claim 1, wherein the second material comprises a polymer.

14. The device of claim 1, wherein the second material comprises a colorant.

15. The device of claim 1, wherein the first material comprises a compatibilizing material.

16. The device of claim 1, further comprising a discrete strip of a third material encapsulated by the first material when the balloon is inflated, the third material being a different material when the balloon is inflated, the third material being a different material than the first and second materials.

17. The device of claim 16, wherein no cutting element is centered over the discrete strip of the third material.

18. The device of claim 1, wherein the discrete strip of the second material extends continuously from a first end of the balloon proximate the first sleeve portion of the balloon to a second end of the balloon proximate the second sleeve portion of the balloon such that the discrete strip of the second material extends through each of the first sleeve portion, the first tapered portion, the body portion, the second tapered portion, and the second sleeve portion.

19. A medical device, comprising:
    a catheter;
    a repeatable inflatable and deflatable balloon carried by the catheter, the balloon including a body portion, a first sleeve portion, a second sleeve portion, a first tapered portion located between the first sleeve portion and the body portion, and a second tapered portion located between the second sleeve portion and the body portion, the balloon formed having a first material and a discrete striped portion encapsulated by the first material when the balloon is inflated, the discrete striped portion extending continuously along the body portion of the balloon, at least a portion of the first tapered portion, and at least a portion of the second tapered portion, the discrete striped portion having a lower distensibility and a higher stiffness than the first material of the balloon; and
    a cutting element carried by the balloon centered over the discrete striped portion;
    wherein portions of the balloon formed of the first material that are adjacent to the discrete striped portion form flaps each time the balloon is deflated such that the cutting element is located in a furrow between flaps of the balloon.

20. The device of claim 19, wherein the balloon is formed having a plurality of striped portions.

21. The device of claim 20, wherein the number of striped portions is greater than the number of cutting elements carried by the balloon.

22. The device of claim 20, wherein the striped portions are equally spaced around the circumference of the balloon.

23. The device of claim 19, wherein the striped portion extends parallel to the longitudinal axis of the balloon.

24. The device of claim 19, wherein the balloon is formed by co-extrusion.

25. The device of claim 19, wherein the balloon is a multi-layered balloon.

26. The device of claim 19, wherein the striped portion extends continuously along the length of the balloon.

27. The device of claim 19, wherein the striped portion has a distensibility less than about 1 mm along the length of the balloon over a predetermined pressure range.

28. The device of claim 19, wherein the striped portion has a distensibility less than about 0.8 mm along the length of the balloon over a predetermined pressure range.

29. The device of claim 19, wherein the striped portion has a distensibility less than about 0.5 mm along the length of the balloon over a predetermined pressure range.

30. The device of claim 19, wherein the striped portion has a distensibility less than about 0.3 min along the length of the balloon over a predetermined pressure range.

31. The device of claim 19, wherein the striped portion has a distensibility less than about 10% along the length of the balloon over a predetermined pressure range.

32. The device of claim 19, wherein the striped portion has a distensibility less than about 7% along the length of the balloon over a predetermined pressure range.

33. The device of claim 19, wherein the striped portion has a distensibility less than about 5% along the length of the balloon over a predetermined pressure range.

34. The device of claim 19, wherein the striped portion comprises a liquid crystal polymer.

35. The device of claim 19, wherein the striped portion comprises a colorant.

36. The device of claim 19, wherein the balloon comprises an inorganic additive.

37. The device of claim 19, wherein the striped portion extends over a portion of the length of the balloon.

38. The device of claim 19, wherein the striped portion extends over substantially the entire length of the balloon.

39. The device of claim 19, wherein the cutting element is spaced from the striped portion.

40. The device of claim 19, wherein the striped portion comprises a polymer.

41. The device of claim 19, wherein the striped portion comprises a colorant.

42. The device of claim 19, wherein the first material comprises a compatibilizing material.

43. The device of claim 19, further comprising a second discrete striped portion encapsulated by the first material when the balloon is inflated, the second discrete striped portion being formed of a different material than the first material and the discrete striped portion.

44. The device of claim 43, wherein no cutting element is centered over the second discrete striped portion.

45. The device of claim 19, wherein the discrete striped portion extends continuously from a first end of the balloon proximate the first sleeve portion of the balloon to a second end of the balloon proximate the second sleeve portion of the balloon such that the discrete striped portion extends through each of the first sleeve portion, the first tapered portion, the body portion, the second tapered portion, and the second sleeve portion.

46. A medical device, formed by a method comprising:
forming a tube having a discrete striped portion encapsulated by a first material, the discrete striped portion extending continuously from a first end of the tube to a second end of the tube, the discrete striped portion having a lower distensibility and a higher stiffness than the first material of the tube;
forming a repeatably inflatable and deflatable balloon from the tube, the balloon including a body portion, a first sleeve portion proximate a first end of the balloon, a second sleeve portion proximate a second end of the balloon, a first tapered portion located between the first sleeve portion and the body portion, and a second tapered portion located between the second sleeve portion and the body portion, the discrete striped portion being encapsulated by the first material when the balloon is inflated, and the discrete striped portion extending continuously from the first end of the balloon to the second end of the balloon such that the discrete striped portion extends through each of the first sleeve portion, the first tapered portion, the body portion, the second tapered portion, and the second sleeve portion;
attaching a cutting element to the balloon centered over the discrete striped portion; and
folding the balloon such that each time the balloon is deflated, the cutting element is located in a furrow of the balloon between flaps of the balloon formed of the first material which are adjacent to the discrete striped portion.

47. The device of claim 46, wherein the attached cutting element is spaced from the striped portion.

48. The device of claim 46, wherein the striped portion comprises a polymer.

49. The device of claim 46, wherein the striped portion comprises a colorant.

50. The device of claim 46, wherein the first material comprises a compatibilizing material.

51. The device of claim 46, further comprising a second discrete striped portion encapsulated by the first material when the balloon is inflated, the second discrete striped portion being formed of a different material than the first material and the discrete striped portion.

52. The device of claim 51, wherein no cutting element is centered over the second discrete striped portion.

* * * * *